United States Patent [19]
Weinberg

[11] Patent Number: 5,484,472
[45] Date of Patent: Jan. 16, 1996

[54] MINIATURE AIR PURIFIER

[76] Inventor: Stanley Weinberg, 575 Tigertail Rd., Los Angeles, Calif. 90049

[21] Appl. No.: 384,511

[22] Filed: Feb. 6, 1995

[51] Int. Cl.⁶ ........................................................ B03C 3/32
[52] U.S. Cl. ........................ 96/26; 55/356; 96/55; 96/68; 96/69; 96/80; 96/97; 96/98; 323/903; 361/226; 361/235
[58] Field of Search ............................. 96/97, 80, 26, 96/55, 59, 68, 69, 80, 97, 98, 66; 55/356, 357; 95/70, 78, 80, 81; 422/4, 22, 120, 121; 323/903; 361/226, 233, 235

[56] References Cited

U.S. PATENT DOCUMENTS

| | | | |
|---|---|---|---|
| Re. 33,927 | 5/1992 | Fuzimura | 96/98 X |
| T868,006 | 11/1969 | Shutack | 55/356 X |
| 2,067,822 | 1/1937 | Biederman | 96/65 X |
| 3,295,440 | 1/1967 | Rarey et al. | 96/97 X |
| 4,227,894 | 10/1980 | Proynoff | 96/55 |
| 4,244,710 | 1/1981 | Burger | 96/97 X |
| 4,253,852 | 3/1981 | Adams | 96/58 |
| 4,402,716 | 9/1983 | Chiaramonte | 55/356 |
| 4,477,263 | 10/1984 | Shaver et al. | 361/235 X |
| 4,592,763 | 6/1986 | Dietz et al. | 96/80 X |
| 4,670,026 | 6/1987 | Hoenig | 96/97 X |
| 4,689,715 | 8/1987 | Halleck | 361/235 X |
| 4,789,801 | 12/1988 | Lee | 96/26 X |
| 4,911,737 | 3/1990 | Yehl et al. | 95/81 |
| 5,034,032 | 7/1991 | Yikai et al. | 96/97 X |
| 5,055,115 | 10/1991 | Yikai et al. | 96/97 X |
| 5,065,272 | 11/1991 | Owen et al. | 96/97 X |
| 5,159,544 | 10/1992 | Hughey et al. | 323/903 X |
| 5,322,550 | 6/1994 | Park | 96/66 |
| 5,332,425 | 7/1994 | Huang | 96/26 |
| 5,407,469 | 4/1995 | Sun | 361/226 X |

FOREIGN PATENT DOCUMENTS 931625  7/1963  United Kingdom ...................... 96/80

OTHER PUBLICATIONS

Wein Products, Inc. Brochure, Los Angeles, Calif., Undated.
Wein Products, Inc. Brochure, "Air Supply VI–350M", Los Angeles, Calif., undated.

Primary Examiner—Richard L. Chiesa
Attorney, Agent, or Firm—Price, Gess & Ubell

[57] ABSTRACT

A small, battery-powered air purifier can be clipped to a wearer's front shirt pocket or worn suspended from a cord about the wearer's neck. The device includes a housing containing a compact circuit that transforms direct current provided by the battery into a negative high voltage pulsating current which is connected to a sharp metal point contained within a chamber inside the hollow housing. A corona discharge forms on the sharp point, ionizing air molecules and any particulates, and generating ozone. An opening into the chamber is covered by a noncorrosive metal grid connected to the positive terminal of the battery. The negative ions are attracted to this grid, thereby completing an electrical circuit. Movement of the ions to the grid results in mass movement of air which causes a stream of air to emerge through the grid. As the air passes the grid, negatively charged particulates are deposited on the grid. The cleansed air stream, containing traces of ozone and negative ions, can be directed to flow across the face of the user, thereby limiting the contact of contaminated ambient air with the eyes and nasal passages of the user. An activated charcoal filter pad can be attached to the device to interact with the cleansed air stream to reduce the ozone level.

21 Claims, 2 Drawing Sheets

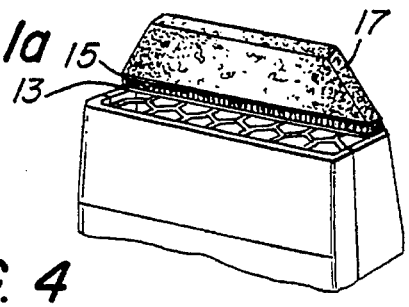
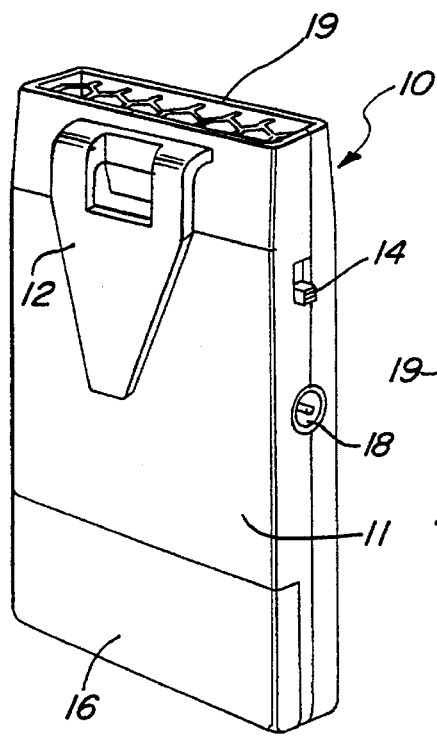
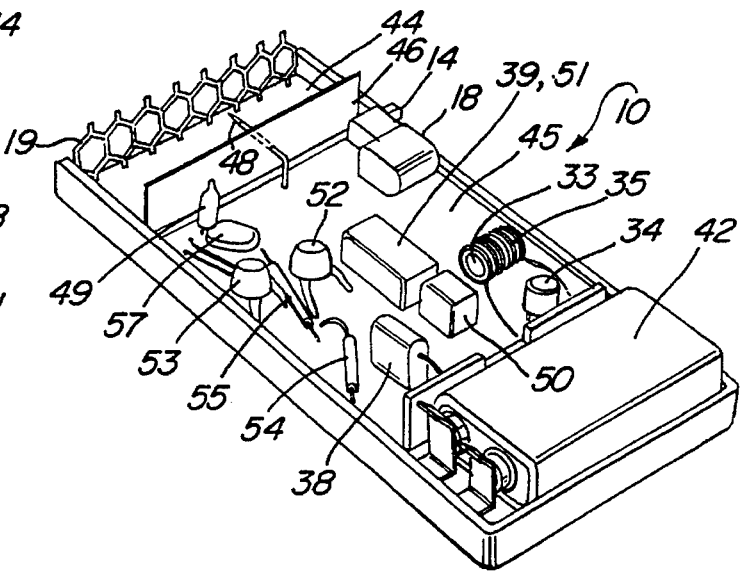
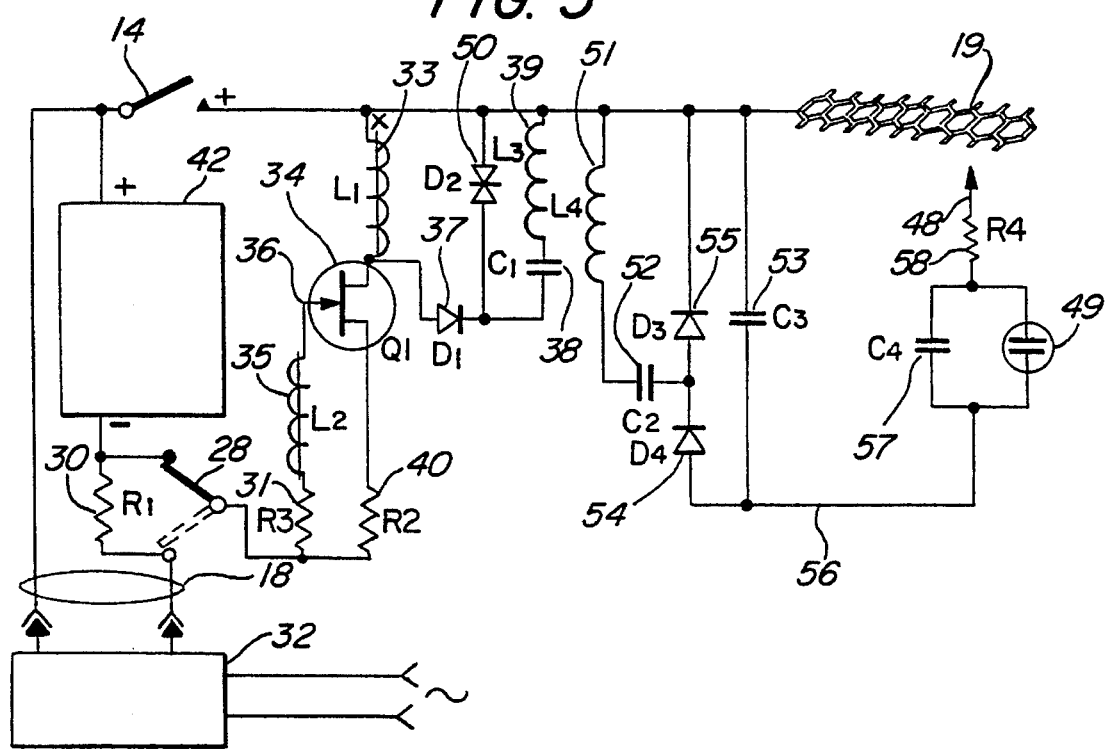

MINIATURE AIR PURIFIER

BACKGROUND OF THE INVENTION

1. Field of the Invention

The present invention involves the field of electronic air purification and, more specifically, a miniature device that generates and circulates ionized and ozonated air around an individual's face.

2. Description of Related Art

Ever since humans first began to live in enclosures instead of outdoors like wild animals, they have been faced with problems of indoor air pollution. At the very least, a building impedes fresh air flow and traps various potentially noxious substances and airborne disease organisms. Originally, a major source of noxious airborne substances was smoke from indoor fires intended to heat the dwelling and cook food. Eventually, chimneys and similar devices were developed to conduct most of the smoke safely to the outdoors.

Over time various other heating and cooling technologies were perfected to further improve the quality of indoor air. It seems that today we have almost come full circle. The outdoor air, at least in most major cities, is saturated with pollutants resulting from automobile exhaust and manufacturing activities. At the same time, escalating energy costs have resulted in "energy efficient" buildings which reduce heating and cooling costs by reducing the amount of outdoor air allowed to enter the building. To make matters worse, many modern materials used in building materials and furniture outgas toxic or irritating vapors. With less outdoor air entering to dilute these outgassed toxins, the building air can become extremely unpleasant or even unhealthful to breath.

There have been a wide variety of attempts to deal with problems of "indoor air pollution" or the "sick building syndrome," as this problem is sometimes called. Specialized air filters have been applied to central air systems in an effort to cleanse the air. Smaller room-sized filtering systems have also been employed. Elaborate heat exchangers have been added to air intakes so that more air can be exchanged with the outside without a great loss of energy. Unfortunately, such solutions are expensive to employ and are often not undertaken until air quality problems become critical.

Ultimately the solution to indoor air pollution lies in improved building designs, improved construction materials, and improved control of outdoor air pollution. But in the meantime, many people are stuck in buildings that have inadequate air quality. Sensitive individuals are especially impacted by poor air quality and may need to employ special devices to ameliorate indoor air quality.

One popular approach has been the use of negative ion or ozone generators. The basis for such devices is relatively simple. Generally, they employ a high voltage electrical source to produce a corona discharge which negatively charges air molecules and particulates suspended in the air. At the same time, some of the oxygen molecules ($O_2$) in the air are converted into a more reactive compound, ozone ($O_3$). The negatively charged particulates generally interact with neutral or positively charged surfaces and "precipitate" from the air, thus resulting in a reduction in the number of particulates. Ozone tends to react with various airborne organic molecules, often destroying them or rendering them less toxic. Ozone may also destroy airborne disease organisms. Finally, there is some evidence that negative ions in the air may promote psychological and/or physical well being. Certainly, the clean smell and feel of the air following an electrical storm is at least partly due to the presence of ozone and negative ions.

One problem with many negative ion generating systems is that they are fairly large and require a source of electrical power such as a wall plug. Thus, the units are not portable and, while such a unit may cause a localized region of improved air quality, it does little for a sensitive individual who must frequently move from room to room. In addition, it is somewhat difficult to direct the ionized air. In most systems the ionized air simply diffuses into the room. A few systems contain fans to direct the ionized air, but fans tend to increase the bulk and complexity of the devices. There have also been some efforts to produce "portable" units that can be carried about by an individual, but these "portable" units have actually weighed in the neighborhood of five pounds.

OBJECTS AND SUMMARY OF THE INVENTION

Therefore, it is an object of the present invention to provide a truly portable negative ion/ozone generator that an individual can easily move from room to room;

It is an additional object of the present invention to provide a portable negative ion/ozone generator that is sufficiently small to be worn as an unobtrusive portion of one's apparel;

It is yet another object of the present invention to provide a portable negative ion/ozone generator that is very energy efficient and gives a long period of operation from a battery or other direct current power source; and It is a further object of the present invention to provide a portable negative ion/ozone generator that is capable of producing a sufficient air flow to distribute the ionized air and can, thereby, act to prevent particulates and contaminants from reaching the face of a user wearing the device.

These and other objects are met by a small, battery-powered device that can be clipped to a wearer's front shirt pocket or worn suspended from a cord about the wearer's neck. The device comprises a housing containing a compact circuit that transforms direct current provided by the battery into a negative high voltage pulsating current connected to a sharp metal point enclosed within the hollow body of the housing. A corona discharge forms on the metal point, ionizing air molecules and any particulates, and generating ozone. An opening into the hollow body of the device is covered by a metal grid connected to the positive terminal of the battery. The negative ions are attracted to this grid to complete an electrical circuit. Movement of the ions results in mass movement of air causing a stream of air to emerge through the grid. As the air passes the grid, negatively charged particulates are deposited on the grid. The cleansed air stream, containing traces of ozone and negative ions, can be directed to flow across the face of the user, thereby limiting the contact of contaminated ambient air with the eyes and nasal passages of the user.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 shows a perspective drawing of the device of the present invention;

FIG. 1a shows the device with a removably attached small filter pad;

FIG. 3 is a diagram of the electronic circuitry of the preferred embodiment of the present invention; and FIG. 4 shows the device with the housing opened to reveal inner components.

DETAILED DESCRIPTION OF THE PREFERRED EMBODIMENTS

Figure 2A:
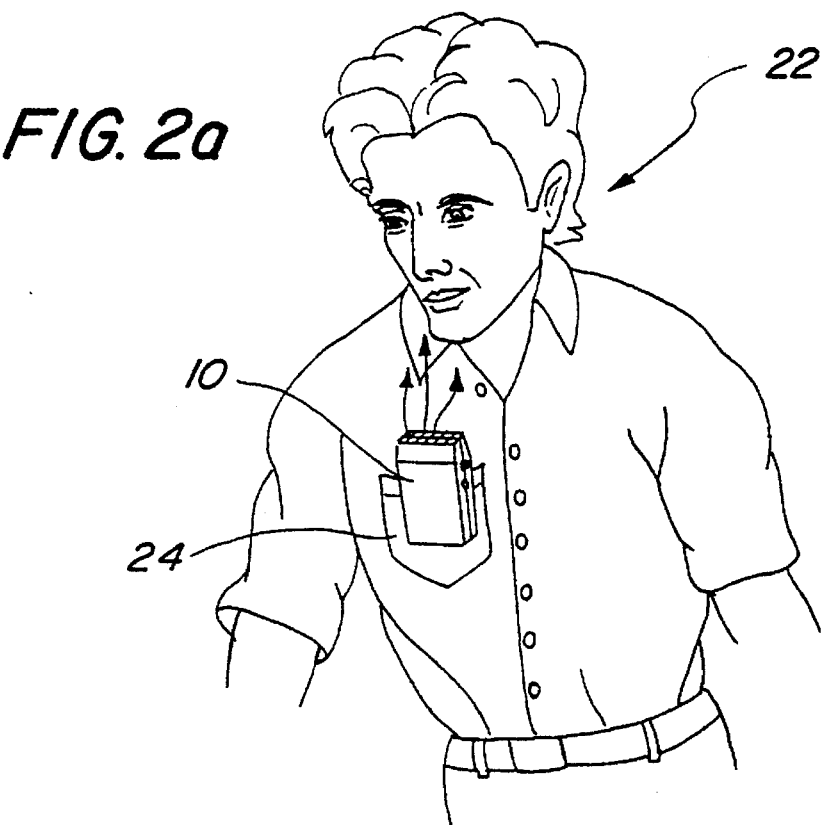
FIGS. 2a, and 2b illustrate the device of the present invention in use being worn by an individual.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a portable personal negative ion/ozone generator.

A difficulty in creating a personal negative ion/ozone generator is to produce a unit that is small enough to be conveniently carried or worn on a user's person. Such a device must have a self-contained power source, such as a battery, and be capable of operating for a reasonably long time on that battery. The notion behind negative ion/ozone generators is that the air will be purified by electrostatic dust precipitation (electrically charged particulates in the air become attracted to neutral or positively charged objects) and by destruction of pollutants and airborne disease organisms through reaction with ozone.

One method of ionizing air and producing ozone is to establish a corona discharge. Corona discharges occur when a surface contains an excess of electrons at a sufficiently high negative potential that surrounding air molecules take up electrons and become ionized. As the ionized atoms undergo changes in energy level, the gas emits light so the discharge is frequently visible as a faint blue glow. Although any surface may be used to create a corona discharge, pointed surfaces are most effective. Natural corona discharges are often visible during electrical storms when pointed objects such as lightning rods can be seen to glow. In the days of sailing ships corona discharges from the tips of masks were known as St. Elmo's Fire, and the eerie blue "flames" were regarded with superstitious dread by sailors.

An ionizing source large enough to produce an effective concentration of ozone and negative ions is necessary. At the same time, excessive ozone can be irritating to one's lungs and mucus membranes. Furthermore, voltages sufficiently high to support a corona discharge can impart an unpleasant static electrical shock. Therefore, the discharge must be kept away from the user's touch. Finally, means must be provided to move the purified air into the vicinity of the user's nose. The present invention provides a unique solution to these and related problems.

A miniature electronic circuit is used to transform battery voltage into a sufficiently high negative potential to effect a corona discharge. The negative potential is conducted to a metallic needle point where a corona discharge occurs. This emitter point is contained within a chamber in the device so that a user can never come into contact with the high voltage. As the corona discharge occurs, electrons, originally generated by the electrochemical reaction of the battery, are transferred to air molecules. An electric circuit is completed by placing a conductive grid placed near the emitter point and connected to the battery.

The conductive grid has several important purposes. First, the grid captures many of the negative ions and provides a surface on which charged particulates can precipitate. Because the grid should be easily cleaned of precipitated particulates and because ozone is reactive, the grid should be constructed of, or plated with a conductive and nonreactive metal such as nickel, gold, silver, chromium, rhodium or platinum. Currently the preferred choice is a steel grid with a nickel plating.

Second, the migration of negative ions moving from the emitter point to the grid causes a mass flow of air molecules. This flow exits through the grid and blows in whatever direction the grid is aimed. As elaborated below, grid structure and placement is critical to produce maximum air flow. In a unit with proper grid structure and placement air flow rates of 100 ft/min have been measured with a Dwyer vanometer.

The unit creates a significant net flow of air without any moving mechanical parts. This air flow can deliver purified air to the face of the user, thereby shunting away contaminants in the ambient air. Furthermore, this constant flow of air dilutes the ozone so that there can be an effective concentration of ozone in the vicinity of the emitter point within the device, while the ozone concentration six inches from the device has been diluted to about 0.04 ppm, a level which OSHA considers as safe.

FIG. 1 shows a perspective view of the entire device 10. The unit comprises a rectangular shaped housing 11 about the size of an average shirt pocket. The exact size and shape is unimportant. The unit should be small enough and light enough to be conveniently attached to a user's clothing. A clip 12 is provided for this purpose. Alternatively, a cord 22 can be looped through the clip 12 so the device can be worn around the user's neck (see FIG. 2b).

A small slide switch 14 controls the power from a 9-volt battery 42 that is contained within a battery compartment 16 at one end of the device. The battery can be easily replaced by opening a battery compartment door. A connector 18 for an AC adaptor is also provided. This adaptor allows the device to be operated from house current, and also recharges a nickel cadmium battery if such a battery is installed.

A conductive grid 1.9 is located at the opposite end of the unit 10 from the battery compartment 16. This grid 19 forms the top of an ionization chamber 44 located within the device 10. As shown in FIG. 4, this chamber 44 is formed by the walls of the housing 11, the grid 19, and a membrane barrier 46 which lies between the chamber 44 and an electronics board 45. A point emitter 48, comprising a metallic needle, penetrates the membrane barrier 46 to connect to the electronics board 45. A neon gas-discharge lamp 49 is located at one edge of the membrane barrier 46 and is visible by looking through the grid 19 from the grid end of the device 10.

Figure 2B:
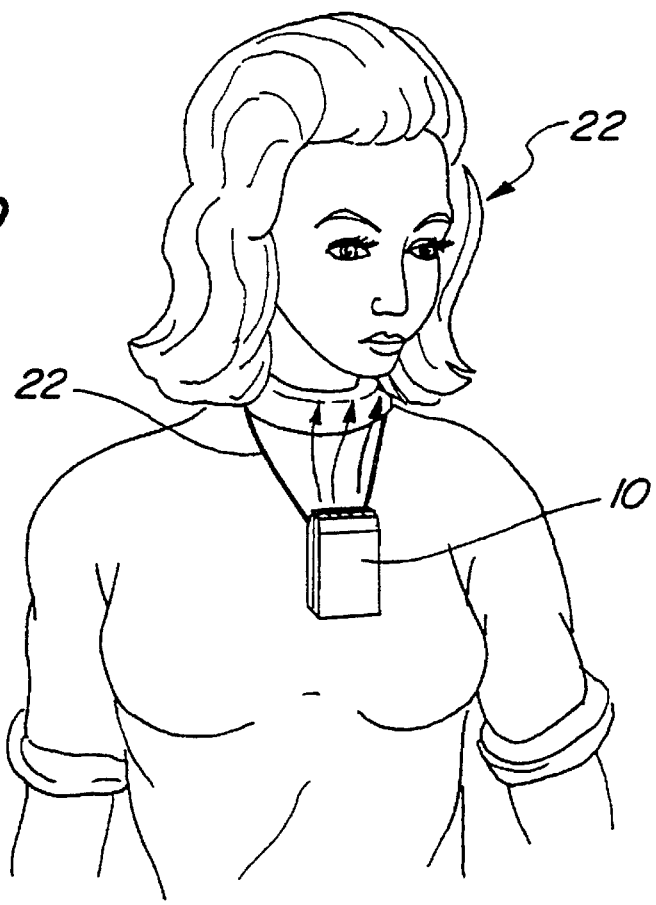

When the device 10 is operational, a corona discharge occurs at the emitter point 48, thereby ionizing the air and forming ozone. The negative ions so formed are attracted to the conductive grid 19, which is also connected to the battery 42, causing a mass flow of air (arrows, FIGS. 2a and 2b) towards and through the grid 19. FIGS. 2a and 2b show the device 10 in use being worn clipped to a front shirt pocket 24 or hung about the neck of a user 22. The mass flow of ionized air propels a stream of air upward and towards the face of the user 22. At the same time, replacement air is drawn into the ionization chamber 44 through the edges of the grid. 19, where it, too, becomes ionized and accelerated towards the grid 19 and out of the unit 10.

The structure of the grid 19 and its placement relative to the emitter point 48 is critical for attaining a maximum air flow. It has been discovered that the grid 19 must have adequate open areas so that air circulation is not impeded. At the same time there must be sufficient surface area for adequate ion interaction and particulate precipitation. Grids with about 80% open space are preferred. Grids with a considerably larger percentage of open space would tend to have inadequate charged area and would also be excessively fragile. Similarly grids with a considerably smaller percentage of open space tend to excessively impeded the mass air flow.

The grid opening geometry is also important. The preferred grid 19 has hexagonal openings with a diameter of about one quarter inch. Screens with similarly-sized circular or square openings should also work effectively. Grids with considerably smaller openings excessively impede the air flow and are fragile. Grids with .much larger openings do not effectively present charged surfaces for attracting ionized air and charged particulates.

Finally, there is an important interaction between grid geometry and opening and distance from the emitter point 48. If the grid 48 is too close to or too far from the emitter point 48, the velocity of the accelerated air is considerably slowed. Each different grid configuration has a somewhat different ideal distance from the grid 19 to the emitter point 48. With the preferred grid geometry, as described above, the emitter point 48 produces a maximal air flow when it is about 0.3 inches from the grid 19.

In the ionization chamber 44 a relatively high concentration of ozone inactivates pollutants and microbes, many of which are drawn to and captured by the grid 19. The flow of purified air past the face of the user 22 prevents many contaminants in the ambient air from ever reaching the nasal passages of the user.

A small filter pad 17, trapezoidal in outline, as shown in FIG. 1a, which contains activated charcoal can be removably attached to the unit 10 by mating of a hook-and-loop system (VELCRO™) 15, 13. When installed, the filter pad 17 forms approximately a 45-degree angle with the metal grid 19. Because the filter pad 17 is trapezoidal, it does not interact with the air stream near the edges of the grid 19. This allows the replacement air to enter the ionization chamber 44 unimpeded. However, the ionized air exiting the center of grid 19 strikes the filter pad 17. The filter pad absorbs ozone, as well as organic pollutants, from the air. The filter pad 17 directs the purified air stream somewhat away from the user's face in case the user is especially sensitive to even residual levels of ozone. The filter pad 17 can be easily flipped over, exposing a fresh surface to the ionized air stream. After both surfaces are exhausted, a fresh filter pad is installed.

FIG. 3 shows miniature electronic circuitry located on the electronics board 45. The purpose of the circuitry is to transform the low voltage, relatively high current source of the 9-volt battery 42 into high voltage (about 15,000 volts) at a low current to effect ionization at the emitter point 48. Essentially, the circuit is a switching step-up power supply. The slide switch 14 switches the power on and off. If an optional AC adaptor 32 is installed, a connector switch 28 that is part of the connector 18 interposes a first resistor 30 ($R_1$) between the AC adaptor 32 and the battery 42 to provide a trickle charge. The position of the connector switch 28 with the adapter 32 attached is shown dotted in FIG. 3.

When the slide switch 14 is closed, current from the positive pole of a current source, either the battery 42 or an optional AC adaptor 32, if it is attached to the device, flows through a first coil 33 ($L_1$), through a depletion mode metal oxide field effect transistor (MOSFET) 34 ($Q_3$), and through a second resistor 40 ($R_2$), with a preferred value of 10 ohms, to return to the current source. A high voltage (600 V) MOSFET such as BSS135 is preferentially employed for $Q_1$, which acts as a switch.

The coil 33 ($L_1$) has an inductance of about 10 mH. As the current flows through the coil 33, a magnetic field forms and expands. The magnetic field intersects the windings of a second coil 35 ($L_2$) which surrounds the first coil 33. This changing magnetic field induces a voltage in the second coil 35. One leg of the second coil 35 is attached to the negative pole of the current source through a third resistor 31 ($R_3$, 1.2 k ohm), while the other leg is attached directly to a gate 36 of the MOSFET 34. The third resistor 31 protects the gate 36 from excessive current flows.

The third resistor 31 normally holds the gate 36 negative. The MOSFET 34 conducts slightly operating in a constant current mode in a "pinched off" region. The second resistor 40 maintains the MOSFET in the "pinched off" region, thereby improving the sharpness of the switching and reducing the overall current drain of the circuit. However, the slight current flow in the first coil 33 induces a voltage in the second coil 35 temporarily overcoming the negative gate voltage. The gate 36 becomes briefly positive, causing the MOSFET 34 to conduct significantly. The magnetic field in the first coil 33 then increases, until it reaches a plateau, at this point the induced voltage disappears allowing the gate 36 to go negative, and causing the MOSFET 34 to return to conducting minimally, the magnetic field surrounding the first coil 33 collapses and the entire process starts over. Thus, the MOSFET/coil arrangement acts as an oscillator, known in the art as a blocking oscillator with a flyback transformer, which rapidly turns the current flow in the first coil 33 on and off.

Each time the magnetic field surrounding the first coil 33 collapses, the magnetic lines of force of the collapsing field interact with the coil's windings to induce a voltage pulse therein. Because the first coil has many windings, the induced voltage pulse has a much higher voltage-about 600 V—than does the battery 42. A first diode 37 ($D_1$) and a first capacitor 38 ($C_1$) form a path between the first coil and the positive pole of the current source.

In a preferred embodiment the first capacitor 38 ($C_1$) has a value of about 0.05 µF, and a diode such as IN4948 or a high efficiency diode such as HER 108 is used as the first diode 37. A third coil 39 ($L_3$) is connected between a first terminal of the first capacitor 38 and the positive pole of the current source. When the MOSFET 34 stops conducting, the high voltage pulse from the first coil 33 passes through the first diode 37 to a second terminal of the first capacitor 38, thereby charging it. As successive voltage pulses reach the first capacitor 38, the voltage potential difference between the second terminal of the capacitor 38 and the positive pole of the current source gradually increases.

A K3000 breakdown diode 50 ($D_2$) with a breakdown voltage of 350 V is connected between the second terminal of the first capacitor 38 and the positive pole of the current source. When the first capacitor 38 has charged to 350 V, the breakdown diode 50 suddenly begins to conduct discharging the first capacitor 38, thereby causing a voltage pulse through the third coil 39. The third coil 39 is actually the primary winding of an auto step-up trigger coil whose secondary coil comprises a fourth coil 51 ($L_4$).

As the 350 V pulses pass through the third coil 39, they induce high voltage pulses of about 15,000 V in the fourth coil 51. Actually, the high voltage pulses are induced with one polarity as the third coil 39 is energized (expanding magnetic field), and with an opposite polarity when the current flow through the third coil 39 ends (collapsing magnetic field).

The fourth coil 51 is connected to two 200 pF, 15 kV capacitors 52 ($C_2$) and 53 ($C_3$) through two high voltage diodes 55 ($D_3$) and 54 ($D_4$) arranged so that the reversing high voltage pulses alternately charge one and then the other of the two capacitors. This results in a negative potential of about 15,000 V in an emitter leg 56 of the circuit. The conductive needle comprising the emitter point 48 is connected to the emitter leg 56 through a fourth resistor 58 ($R_4$) which, in turn, is connected to a neon gas-discharge lamp 49 and a fourth capacitor 57 ($C_4$) connected in parallel to constitute a relaxation oscillator. The fourth resistor 58 preferably has a value of 22 megaohms and acts as an ion current limiting resistor both to protect the user from shock and to protect the MOSFET 34 from an excessive current flow should a conductive object be inserted through the grid 19. This configuration results in the neon lamp 49 visibly pulsating to give an indication of the high voltage corona discharge occurring on the emitter point 48. The pulse rate of the neon lamp 49 is a direct monitor of the rate of negative ion production. A weakening of the battery 42 can be detected as a lowering of the pulse rate.

As mentioned above, the emitter point 48 is located within the housing 11 of the device 10 in the ionization chamber 44. The opening to this chamber is covered by the metal grid 19 which is connected to the positive pole of the current source. Thus, ionized air molecules and ionized particulates are attracted to the grid 19 where they give up electrons to complete the circuit. The particulates remain attached to the grid 19 thus creating a need to occasionally clean off the grid 19. At the same time, this flow of ions creates a mass flow of air which propels a stream of purified, ozonated air in whichever direction the device is pointed.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A portable air purifier comprising:

a housing sized to be readily carried on the person of a user;

a battery, disposed within the housing, for supplying a low voltage;

circuit means connected to the battery for transforming the low voltage into a sufficiently high voltage to support a corona discharge;

an ionization chamber within the housing and having an opening to the outside of the housing;

a needle point emitter for creating a corona discharge, the needle point emitter disposed within the ionization chamber and electrically connected to the circuit means; and an electrically conductive grid over the opening between the ionization chamber and the outside of the housing, said grid connected to the battery so that when the corona discharge occurs at the needle point emitter, negatively charged ions produced by the corona discharge are attracted to said grid, completing an electrical circuit and thereby causing a mass flow of air which produces an emerging air current flowing through said grid and out of the ionization chamber.

2. The air purifier of claim 1, wherein a neon gas-discharge lamp and a capacitor are electrically connected in parallel between the needle point emitter and the circuit means to form a relaxation oscillator, whereby operation of the corona discharge is signified by visible pulsations of the neon lamp, said pulsations being proportional to ion flow.

3. The air purifier of claim 1, further comprising a filter pad removably attachable to the housing and, when attached, disposed to interact with the air current emerging through the grid.

4. The air purifier of claim 1, wherein said grid has a noncorroding surface selected from the group of metals consisting of: nickel, gold, silver, platinum, chromium, and rhodium.

5. The air purifier of claim 1, wherein a distance between said grid and the needle point emitter, a percentage of opening of said grid, and a size of openings in said grid selected so as to maximize the emerging air current, the distance between the grid and the needle point emitter being about 0.3-inch and the percentage of opening of the grid being about 80%.

6. A portable air purifier comprising:

a housing sized to be readily carried on the person of a user;

a battery, disposed within the housing, for supplying a low voltage;

circuit means connected to the battery for transforming the low voltage into a sufficiently high voltage to support a corona discharge;

an ionization chamber within the housing and having an opening to the outside of the housing;

a needle point emitter for creating a corona discharge, the needle point emitter disposed within the ionization chamber and electrically connected to the high voltage; and an electrically conductive grid over the opening between the ionization chamber and the outside of the housing, said grid connected to the battery so that when the corona discharge occurs at the needle point emitter, negatively charged ions produced by the corona discharge are attracted to said grid completing an electrical circuit and thereby causing a mass flow of air which produces an emerging air current flowing through the grid out of the ionization chamber.

7. The air purifier of claim 6, further comprising a filter pad removably attachable to the housing and, when attached, disposed to interact with the emerging air current.

8. The air purifier of claim 6, wherein said grid has a noncorroding surface selected from the group of metals consisting of: nickel, gold, silver, platinum, chromium and rhodium.

9. The air purifier of claim 6, wherein a distance between said grid and the needle point emitter, a percentage of opening of said grid, and a size of openings in said grid selected so as to maximize the emerging air current.

10. The air purifier of claim 6, wherein a neon gas-discharge lamp and a capacitor are connected in parallel between the needle point emitter and the high voltage to form a relaxation oscillator, whereby the corona discharge is signified by visible pulsations of said neon lamp, said pulsations being proportional to ion flow.

11. The air purifier of claim 6, wherein the circuit means comprises:

a first switching means connected between a negative terminal of the battery and a first terminal of a first coil, a second terminal of said coil being connected to a positive terminal of the battery, for repeatedly interrupting current flow from the battery through the first coil, thereby inducing high voltage pulses in the first coil;

a first charging means for charging a first capacitor from the voltage pulses from the first coil, the first capacitor being operationally connected to a second coil;

a second switching means for discharging the first capacitor through the second coil;

a third coil disposed in relation with the second coil to form a step-up transformer so that discharging the first capacitor through the second coil induces higher voltage pulses in the third coil, the higher voltage pulses being of sufficient voltage to support a corona discharge; and a second charging means for charging a second capacitor from the high voltage pulses of the third coil, thereby providing a corona discharge voltage supply at negative terminals of the second capacitor.

12. The air purifier of claim 11, wherein the first switching means comprises a depletion mode metal oxide field effect transistor connected between the first coil and a negative terminal of the battery, the gate of said transistor being connected to the negative terminal through an inductor which is disposed in magnetic communication with the first coil so that current flow through the first coil induces a voltage in the inductor.

13. The air purifier of claim 11, wherein the second charging means comprises a first high voltage diode connected to charge the second capacitor and wherein the second charging means further comprises a third capacitor and a second high voltage diode connected to charge the third capacitor.

14. The air purifier of claim 11, wherein the second switching means comprises a breakdown diode connected between the positive terminal of the battery and the first capacitor so that the breakdown diode begins to conduct when a predetermined voltage is reached by the first capacitor, resulting in the first capacitor discharging through the second coil.

15. The air purifier of claim 6, wherein the opening comprises substantially all of an end of the housing.

16. A portable air purifier comprising:

a housing sized to be readily carried on the person of a user;

a battery for supplying a low voltage disposed within the housing;

an electrical circuit connected to the battery for transforming the low voltage into a sufficiently high voltage for providing a corona discharge voltage supply;

an ionization chamber within the housing and having an opening to the outside of the housing;

a metal needle point emitter for creating a corona discharge, the metal needle point emitter disposed within the ionization chamber and electrically connected to the corona discharge voltage supply;

a neon gas-discharge lamp and a capacitor connected in parallel, and a current limiting resistor connected between the needle point emitter and the corona discharge voltage supply to form a relaxation oscillator, whereby operation of the corona discharge is signified by visible pulsations of said neon lamp, said pulsations being proportional to ion flow; and an electrically conductive grid over the opening between the ionization chamber and the outside of the housing, said grid connected to the positive terminal battery so that when the corona discharge occurs at the needle point emitter, negatively charged ions produced by the corona discharge are attracted to said grid completing an electrical circuit and thereby causing a mass flow of air which produces an emerging air current flowing through the grid and out of the ionization chamber.

17. The air purifier of claim 16, further comprising a filter pad containing an effective concentration of activated charcoal, said filter pad removably attachable to the housing and, when attached, disposed to interact with the emerging air current.

18. The air purifier of claim 16, wherein a distance between said grid and the needle point emitter, a percentage of opening of said grid, and a size of openings in said grid selected so as to maximize the emerging air current, the distance between the grid and the needle point emitter being about 0.3-inch and the percentage of opening of the grid being about 80%.

19. The air purifier of claim 16, wherein said grid has a noncorroding surface selected from the group of metals consisting of: nickel, gold, silver, platinum, chromium, and rhodium.

20. The air purifier of claim 16 wherein the electrical circuit comprises:

a high voltage depletion mode metal oxide field effect transistor connected between a negative terminal of the battery and a first terminal of a first coil with a gate of said transistor connected through a second coil to the negative terminal of the battery, the second coil being disposed in magnetic communication with the first coil, and a second terminal of the first coil being connected to a positive terminal of the battery, said transistor repeatedly interrupting current flow from the battery through the first coil, thereby inducing high voltage pulses in the first coil.

21. The air purifier of claim 20 wherein the electrical circuit further comprises:

a first diode for charging a first capacitor from the voltage pulses produced by the first coil, a first terminal of the first capacitor being connected to the first diode and a second terminal of the first capacitor being connected to a first terminal of a second coil, a second terminal of the second coil being connected to the positive terminal of the battery;

a breakdown diode connecting the positive terminal of the battery and the first terminal of the first capacitor for discharging the first capacitor through the second coil;

a third coil disposed in magnetic communication with the second coil to form a step-up transformer so that discharging the first capacitor through the second coil induces higher voltage pulses in the third coil, the higher voltage pulses being of sufficient voltage to support a corona discharge; and high voltage capacitors and high voltage diodes connected between a terminal of the third coil and the positive terminal of the battery for charging the capacitors with the voltage pulses produced by the third coil, thereby providing the corona discharge voltage supply.

* * * * *

(12) REEXAMINATION CERTIFICATE (4274th)
United States Patent
Weinberg

(10) Number: US 5,484,472 C1
(45) Certificate Issued: Feb. 20, 2001

(54) MINIATURE AIR PURIFIER

(75) Inventor: Stanley Weinberg, Los Angeles, CA (US)

(73) Assignee: Wein Products Inc., Los Angeles, CA (US)

Reexamination Request:
No. 90/005,695, Apr. 4, 2000

Reexamination Certificate for:
Patent No.: 5,484,472
Issued: Jan. 16, 1996
Appl. No.: 08/384,511
Filed: Feb. 6, 1995

(51) Int. Cl.$^7$ .................................................. B03C 3/32
(52) U.S. Cl. .............................. 96/26; 55/356; 96/55; 96/68; 96/69; 96/80; 96/97; 96/98; 323/903; 361/226; 361/235
(58) Field of Search .............................. 96/26, 97, 55, 96/62, 68, 69, 80, 98, 59, 66; 361/226, 235, 233; 323/903; 55/356, 357; 95/70, 78, 81, 80; 422/4, 22, 121, 120

(56) References Cited

U.S. PATENT DOCUMENTS

| | | | |
|---|---|---|---|
| 3,295,440 | * | 1/1967 | Rarey et al. .......................... 96/97 X |
| 4,227,894 | * | 10/1980 | Proynoff ................................... 96/55 |
| 5,332,425 | * | 7/1994 | Huang ..................................... 96/26 |
| 5,407,469 | * | 4/1995 | Sun ......................................... 96/62 |

FOREIGN PATENT DOCUMENTS

| | | |
|---|---|---|
| 78202380 | 8/1991 | (TW) . |
| 9203863 | 3/1992 | (WO) . |
| 9216251 | 10/1992 | (WO) . |

\* cited by examiner

*Primary Examiner*—Richard L. Chiesa

(57) ABSTRACT

A small, battery-powered air purifier can be clipped to a wearer's front shirt pocket or worn suspended from a cord about the wearer's neck. The device includes a housing containing a compact circuit that transforms direct current provided by the battery into a negative high voltage pulsating current which is connected to a sharp metal point contained within a chamber inside the hollow housing. A corona discharge forms on the sharp point, ionizing air molecules and any particulates, and generating ozone. An opening into the chamber is covered by a noncorrosive metal grid connected to the positive terminal of the battery. The negative ions are attracted to this grid, thereby completing an electrical circuit. Movement of the ions to the grid results in mass movement of air which causes a stream of air to emerge through the grid. As the air passes the grid, negatively charged particulates are deposited on the grid. The cleansed air stream, containing traces of ozone and negative ions, can be directed to flow across the face of the user, thereby limiting the contact of contaminated ambient air with the eyes and nasal passages of the user. An activated charcoal filter pad can be attached to the device to interact with the cleansed air stream to reduce the ozone level.

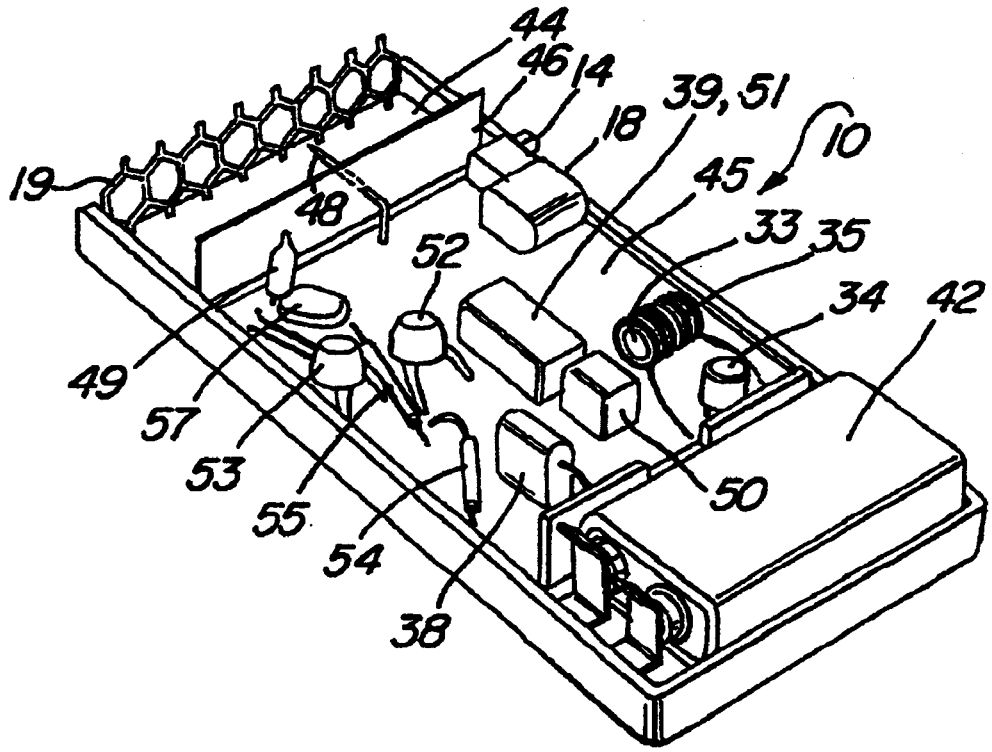

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–21 is confirmed.

* * * * *